United States Patent [19]
Pond et al.

[11] Patent Number: 6,093,020
[45] Date of Patent: Jul. 25, 2000

[54] ATTACHMENT MEANS FOR A DISPOSABLE DENTAL TOOL

[75] Inventors: Gary J. Pond, Racine, Wis.; Michael S. Butler, Round Lake Heights, Ill.

[73] Assignee: Inter-Med, LLC., Racine, Wis.

[21] Appl. No.: 09/346,050

[22] Filed: Jul. 7, 1999

[51] Int. Cl.[7] .............................. A61G 17/02; A61G 5/02; A61C 3/02
[52] U.S. Cl. .................................. 433/80; 433/81; 433/88
[58] Field of Search .................................. 433/80, 81, 216, 433/88, 89, 84, 85

[56] References Cited

U.S. PATENT DOCUMENTS

| | | | |
|---|---|---|---|
| 2,812,765 | 11/1957 | Tofflemire . | |
| 3,164,153 | 1/1965 | Zorzi . | |
| 3,208,145 | 9/1965 | Turner . | |
| 3,593,423 | 7/1971 | Jones | 433/80 |
| 3,624,907 | 12/1971 | Brass et al. . | |
| 3,727,310 | 4/1973 | Baker . | |
| 4,215,476 | 8/1980 | Armstrong | 433/80 |
| 4,340,365 | 7/1982 | Pisanu | 433/80 |
| 4,397,640 | 8/1983 | Haug et al. | 604/33 |
| 4,526,573 | 7/1985 | Lester et al. | 604/33 |
| 4,680,026 | 7/1987 | Weightman et al. | 604/33 |
| 4,872,837 | 10/1989 | Issalene et al. | 433/29 |
| 5,061,180 | 10/1991 | Wiele | 433/91 |
| 5,171,146 | 12/1992 | Guerci | 433/80 |
| 5,468,148 | 11/1995 | Ricks | 433/80 |
| 5,474,450 | 12/1995 | Chronister | 433/80 |
| 5,658,144 | 8/1997 | Tinder et al. | 433/80 |
| 5,716,210 | 2/1998 | Novak | 433/80 |
| 5,772,433 | 6/1998 | Esrock | 433/80 |
| 5,876,201 | 3/1999 | Wilson et al. | 433/80 |
| 5,899,692 | 5/1999 | Davis et al. | 433/80 |

*Primary Examiner*—John J. Wilson
*Assistant Examiner*—Robyn Kieu Doan
*Attorney, Agent, or Firm*—Ryan Kromholz & Manion, S.C.

[57] ABSTRACT

An arrangement for releasably connecting a disposable dental tool to the discharge end of a dental handpiece. The connection includes a plug and socket configuration in which one member includes at least one detent portion arranged to snap fit with an indent portion on the remaining member.

7 Claims, 2 Drawing Sheets

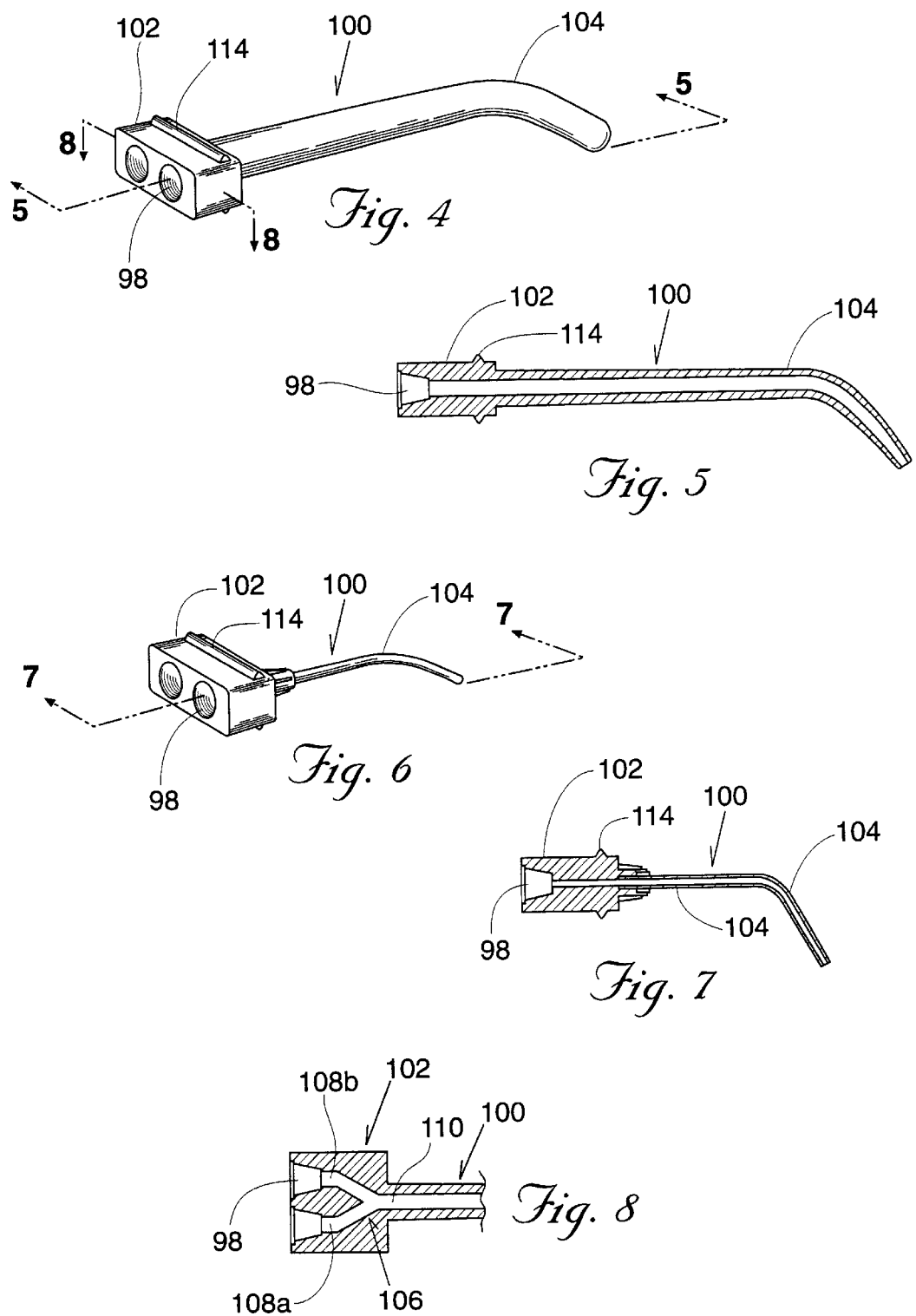

ATTACHMENT MEANS FOR A DISPOSABLE DENTAL TOOL

BACKGROUND OF THE INVENTION

The present invention relates to a dental handpiece, and more particularly to a handpiece that may be used interchangeably as an irrigator, an aerator, an applicator or as an evacuator for treating a patient's mouth.

Past dental practice has included the use of a three-way syringe. An air tube and a water tube join together at a handpiece. Two operating buttons were provided on the handpiece body to allow activation by the dentist of the air or water. By depressing the air button, air flows out of the tip into the appropriate area of the patient's mouth to dry the field of operation. By depressing the water button, a passive flow of water is emitted to clean and float away debris and congestion from the field of operation. By depressing both buttons simultaneously, a spray of air and water may be emitted, which flushes away debris, which can then be vacuumed from the oral cavity using a separate high volume evacuation hand piece.

Later procedures supplied removable air/water tips to allow for sterilization. Prior to that development the tips were disinfected and cleaned by simply wiping them with alcohol. The advancement of supplying removable tips permitted sterilization by means of steam or heat procedures. However, if done with the appropriate frequency, the tips became clogged and unusable in several months.

With the rising incident of communicable diseases, such as hepatitis and acquired immune deficiency syndrome, extreme care is advocated to prevent the transfer of either viral or bacterial infection from one patient to the next. This need has resulted in the use of disposable or throwaway dental tips.

Although dental handpieces have undergone improvements to resolve difficulties encountered by dentists, shortcomings still persist. One such shortcoming is the inability to alternately irrigate, applicate, aerate and evacuate with a single disposable or semi-disposable hand held tool. Examples of the prior art devices have been disclosed in Brass et al. U.S. Pat. No. 3,624,907, Esrock U.S. Pat. No. 5,772,433, and Baker U.S. Pat. No. 3,727,310.

SUMMARY OF THE INVENTION

To overcome the above-identified concerns, the present invention provides a very inexpensive irrigator/applicator/aerator and evacuator arrangement, which may be made entirely disposable. The components making up this arrangement include handpieces, disposable flexible supply lines and a variety of disposable tips to avoid the possibility of contamination. The various components may be made using conventional molding and extrusion techniques from inexpensive materials, both relatively rigid and also very flexible when needed or required.

The dental handpiece of this invention, in a preferred embodiment, comprises an elongated tubular manually held apparatus divided into three portions; namely, a tubular handgrip portion, at least one valve portion and a hollow nozzle support portion. A flexible tube of a relatively small diameter is insertable into the bore of the tubular apparatus and may be fitted to a conventional luer lock member for easy insertion and removal from either an evacuation or an irrigation fluid supply line. Alternatively, the tubular apparatus may be fluidly connected to a medicine supply source. The valve portion is simplistic in structure and may be attached directly with a side opening contacting the tubular bore of the handgrip portion. The valve portion opening is directly engageable with the flexible tube fitted within and longitudinally extending through the bore of the handgrip portion. An applicator tip may be releasably snap fit to the handpiece by way of an attachment means including an adapter plug on one end of the tip and corresponding socket portion on the discharge end of the nozzle portion. The adapter plug is configured to snap fit with the handpiece nozzle support portion which may receive a variety of mating dental fluid supply or evacuation tips.

The attachment means in the preferred embodiment includes a dual entrance socket on the handpiece for receiving the plug portion of a tip. Each socket entrance forms a nozzle support portion that is able to communicate with a corresponding channel in the plug portion to form a "Y" configuration therein. While a symmetric "Y" configuration is preferred, it is within the scope of this invention to include variations of the channels forming the dual entrance end. The plug portion further includes at least one upstanding detent engageable with a corresponding indent area in the socket. This arrangement allows for a facile releasable snap-fit.

DESCRIPTION OF THE DRAWINGS

FIG. 4 is a perspective view of one type of dental tip and showing the plug portion engagement means.

FIG. 5 is a longitudinal sectional view taken along line 5—5 of the tip disclosed in FIG. 3.

FIG. 6 is a perspective view of another type of dental tip and showing the plug portion engagement means.

FIG. 7 is a longitudinal sectional view taken along line 7—7 of the tip disclosed in FIG. 5.

FIG. 8 is an enlarged sectional view of the plug portion of FIG. 4 showing the "Y" channel.

DETAILED DESCRIPTION

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

The term fluid, as used herein, shall be defined as a gas, a liquid, a substance which flows, or a substance which differs from a solid in that it can offer no permanent resistance to change of shape. It shall further include mixtures of gases, mixtures of liquids, and mixtures of gases and liquids.

Figure 1:
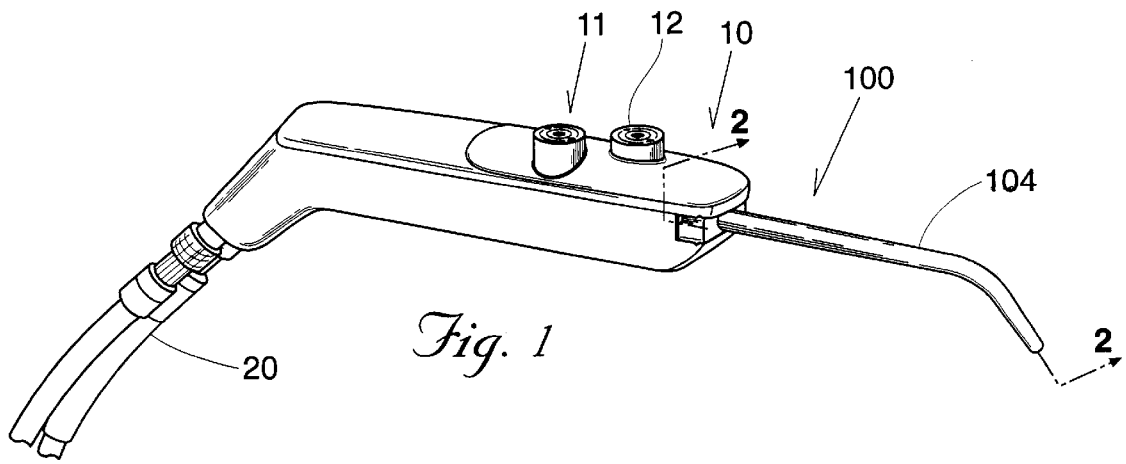
FIG. 1 is a perspective view of an embodiment of a mating tip and dental handpiece made in accordance with present invention.
Figure 2:
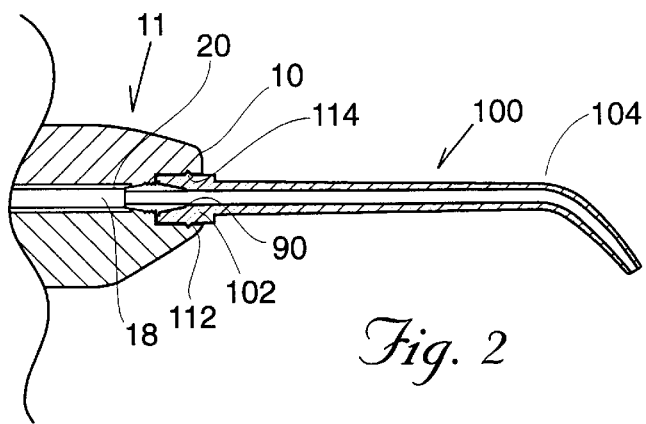
FIG. 2 is a longitudinal sectional view taken along line 2—2 of FIG. 1.
Figure 3:
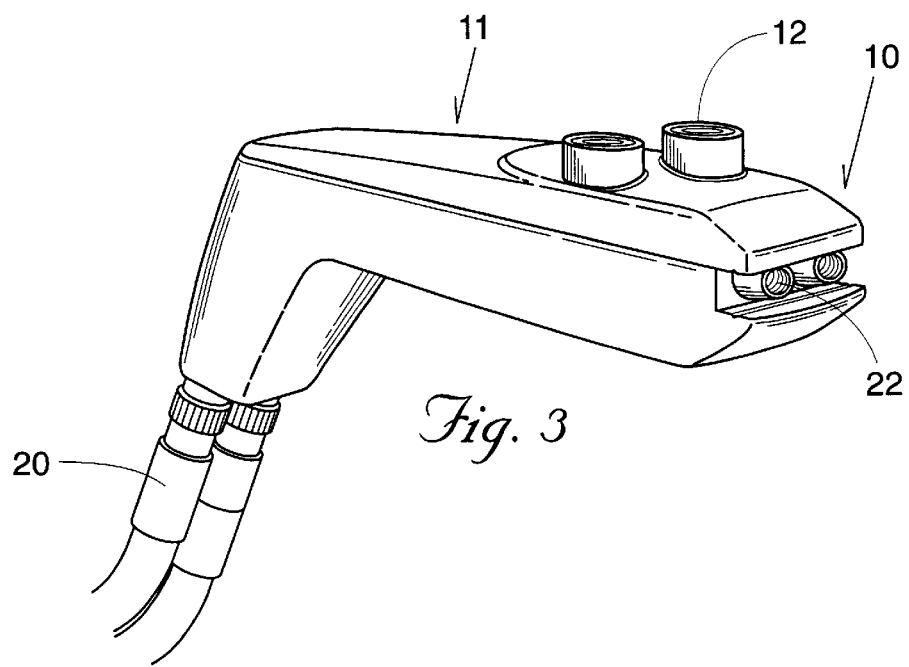
FIG. 3 is a perspective view of the dental handpiece of FIG. 1.

With references to FIGS. 1–3, inclusive, the present invention comprises attachment means for releasably connecting a disposable dental tool, indicated generally by the reference numeral 100 to the discharge end 10 of a dental handpiece 11. The handpiece 11 includes at least one manually operated valve control button 12. As detailed herein, the handpiece includes a pair of valves (not shown) that may independently control fluid flow, such as evacuation and discharge of fluid, through flexible tubing lines 20. As shown in FIG. 2, the handpiece 11 is tubular and includes a coextensive bore 18, which is arranged to receive the elongated, relatively flexible tubing lines 20 which extend through the bore 18. The discharge ends of the flexible tubing lines 20 respectively terminate in nozzles 22 that are adapted to releasably engage a respective opening 98 in the adapter plug portion 102 of tool 100. The opposite ends (not shown) of the tubing 20 are arranged for connection with a vacuum source or, a fluid source, such as water for irrigation, medicine, or to an air-supply. The adapter plug portion 102 of tool 100 further defines a fluid flow channel 106 (seen in FIG. 8) and longitudinally projecting work tip 104. The work tip may be formed from plastic using conventional molding techniques (FIG. 4) or may be partially comprised of a metal tube (FIG. 6). The distal end 10 of handpiece 11 is further comprised of a socket portion 90 which includes at least one indent portion 112.

With particular reference to FIG. 8, it will be noted that the adapter plug portion 102 preferably includes a "Y" shaped fluid flow channel 106. The "Y" shaped configuration includes branches 108*a*, 108*b* and leg 110. The leg 110 of the "Y" shaped channel 106 communicates with the work tip 104. The work tip 104 may be made integrally as shown in FIG. 4 or separately fabricated and joined as shown in FIG. 6. The branches 108*a*, 108*b*, although shown as symmetrical, may also be of unequal length if desired.

As seen in FIGS. 4–7, the plug portion 102 of the tool 100 includes releasable engagement means, preferably comprising at least one upstanding detent 114. Upstanding detent 114 is engageable with a corresponding indent area 112 in the socket portion 90 of the discharge end 10 of handpiece 11 (see FIG. 2). This mating arrangement provides a secure, but releasable, lock fit for the disposable tool 100 while providing removal by a dental practitioner when another tool is desired. This plug-socket arrangement may be utilized with any desired configuration of the tip portion 104, as seen in FIGS. 5 and 7 by way of example.

It will also be apparent that the detent 114 may be formed in the handpiece 11 to engage a mating indent 112 on the plug portion 102.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. Attachment means for releasably securing a disposable tubular dental tool having a bore to a dental handpiece having a discharge end and arranged to receive a pair of tubing lines, and wherein each of said tubing lines terminates at said discharge end, said discharge end including a socket portion, said attachment means including:

a socket portion in said discharge end of said handpiece;

said socket portion having formed therein a pair of protruding nozzles;

each of said nozzles including a bore; and an elongated plug portion at one end of said dental tool, said plug portion arranged to be seated within said socket portion and further being arranged to communicate with a respective nozzle.

2. The attachment means of claim 1 wherein said plug portion includes a Y-shaped fluid flow channel communicated with each of said nozzles and the bore of said dental tool.

3. The attachment means of claim 1 wherein said plug portion and said socket portion include locking means for resisting disengagement of the plug portion from said socket portion and its nozzles.

4. The attachment means of claim 1, wherein said locking means comprises a detent portion engagable with a corresponding indent portion.

5. The attachment means of claim 3, wherein said locking means comprises cooperating, snap-action, detent and indent areas on said socket portion and said plug portion.

6. The attachment means of claim 5, wherein said detent area projects from said plug portion and said indent area is formed in said socket portion.

7. The attachment means of claim 5, wherein said indent area and said detent area are each substantially co-extensive of the length of said plug portion and said socket portion.

* * * * *